(12) United States Patent
Kropp et al.

(10) Patent No.: US 6,339,063 B1
(45) Date of Patent: *Jan. 15, 2002

(54) 9A-AZALIDES AS VETERINARY ANTIMICROBIAL AGENTS

(75) Inventors: Helmut Kropp, Westfield, NJ (US); Daniel Farrington, Spearfish, SD (US); Jeffrey Clark, Middletown, NJ (US); Ronald Ratcliffe, Matawan, NJ (US); Robert Wilkening, Maplewood, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/508,489

(22) PCT Filed: Sep. 4, 1998

(86) PCT No.: PCT/US98/18579

§ 371 Date: May 11, 2000

§ 102(e) Date: May 11, 2000

(87) PCT Pub. No.: WO99/12552

PCT Pub. Date: Mar. 18, 1999

Related U.S. Application Data

(60) Provisional application No. 60/058,330, filed on Sep. 10, 1997.

(51) Int. Cl.$^7$ .................................................. A61K 31/70
(52) U.S. Cl. ........................................................... 514/29
(58) Field of Search ................................. 514/29; 536/7.5

(56) References Cited

U.S. PATENT DOCUMENTS

| | | | | |
|---|---|---|---|---|
| 4,328,334 A | * | 5/1982 | Kobrehel et al. | ............ 536/7.4 |
| 5,332,807 A | | 7/1994 | Waddell et al. | |
| 6,054,434 A | * | 4/2000 | Kropp et al. | ................. 514/29 |

FOREIGN PATENT DOCUMENTS

| | | |
|---|---|---|
| EP | 0 992 509 A2 | 12/2000 |
| WO | WO 94 15617 | 7/1994 |
| WO | WO 9856801 | 12/1998 |
| WO | WO 98 56802 | 12/1998 |

* cited by examiner

*Primary Examiner*—Elli Peselev
(74) *Attorney, Agent, or Firm*—Shu M. Lee; David L. Rose

(57) ABSTRACT

9a-Azalides, and pharmaceutical compositions containing them, are useful in the treatment and prevention of bacterial respiratory and enteric infections in livestock animals, particularly in cattle and swine.

8 Claims, No Drawings

9A-AZALIDES AS VETERINARY ANTIMICROBIAL AGENTS

This application is a 371 of PCT/US98/18579 filed Sep. 4, 1998 which claims the benefit of No. 60/058,330 filed Sep. 10, 1997.

SUMMARY OF THE INVENTION

The present invention provides methods for the treatment or prevention of bacterial respiratory or enteric infections in livestock animals.

BACKGROUND OF THE INVENTION

The morbidity and mortality associated with bacterial respiratory and enteric infections in livestock represent a major economic loss for the animal husbandry industry. In cattle, especially in younger animals, stress as a result of weaning, transportation, dehydration, alteration or deprivation of diet can cause the animals to become highly susceptible to bacterial respiratory infection, especially if the animals are housed in crowded or poorly ventilated quarters. The principal causative bacterial pathogens of bovine respiratory infections are *Pasteurella haemolytica, P. multocida, Haemophilus somnus* and *Mycoplasma* spp. In pigs respiratory infections caused by *Pasteurella multocida* or *Actinobacillus pleuropneumoniae*, and *Mycoplasma* spp. are associated with considerable losses in some herds. The most common causative organisms for enteric diseases in cattle and swine are *Escherichia coli, Treponema hyodysenteriae* and *Salmonella* spp.

The current therapeutic antimicrobial products against respiratory and enteric infections in livestock include a diverse group of older products effective against a broad spectrum of infectious agents, mostly notably among this group are the tetracyclines; and a group of recently introduced products indicated primarily for treatment of bovine respiratory disease, such as quinolones (danofloxacin, enrofloxacin), cephalosporins (cefquinome, ceftiofur), macrolide (tilmicosin), and florfenicol. Resistance to the older antimicrobial agents has developed in the field. Although resistance to the newer products is not yet a problem, it is known that excessive usage favors the emergence of resistance over time, but increasing the numbers of drug families, and thereby mechanisms of action, in use may decrease the probability of resistance development to any individual compound. Thus, there exists a continuing need to discover antimicrobial compounds that are suitable for use in veterinary medicine; preferably, such compounds will belong to a different chemotype from the antimicrobial agents currently in use in animal or human medicine. Other desirable characteristics of a novel antimicrobial product for veterinary use include high potency against target organisms, high target tissue concentration, and long tissue half-life.

9a-Azalides are antibiotics characterized by a 15-membered lactone ring containing a ring nitrogen atom. 9a-Azalides are disclosed in, for example, U.S. Pat. Nos. 4,328,334, 4,517,359, 4,474,768, 4,464,527, 4,526,889, 4,465,674, 4,492,688, 4,512,982, 4,518,590, European Patent Application No. 136,831, European Patent Application No. 259,789, European Patent Application No. 316,128, European Patent Application No. 467,331, European Patent Application 606,062, and European Patent Application 657,464.

U.S. Pat. Nos. 4,474,768, 4,464,527, and 4,526,889 disclose azithromycin, N-ethyl and N-propyl homologs of azithromycin, and 4"-epi-azithromycin, respectively, which are said to be active against *Pasteurella multocida* in vitro; however, the patents also state that regarding the compounds disclosed therein their in vivo activity is more limited as regards susceptible organisms. To Applicants' best knowledge, the known 9a-azalides have not been reported as being clinically useful in the treatment and prevention of bovine or swine respiratory or enteric infections.

DETAILED DESCRIPTION OF THE INVENTION

The present invention provides a method for the treatment or prevention of bacterial respiratory or enteric infection in a livestock animal which comprises administering to a livestock animal in need of such treatment or prevention a therapeutically or prophylactically effective amount of an 9a-azalide.

In a preferred embodiment the 9a-azalide has the formula I:

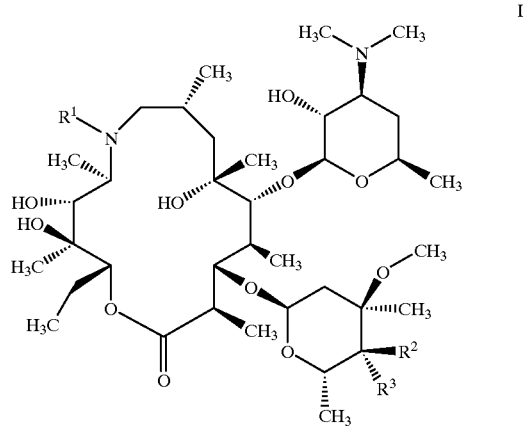

or a pharmaceutically acceptable salt thereof, or a pharmaceutically acceptable metal complexes thereof, and said metal complex is taken from the group consisting of copper, zinc, cobalt, nickel and cadmium; where $R^1$ is hydrogen;

$C_{1-3}$ alkyl optionally substituted by hydroxy, $C_{1-3}$ alkoxy, cyano, $C_{1-3}$ alkoxycarbonyl, halogen, amino, $C_{1-3}$ alkylamino, or di($C_{1-3}$ alkyl)amino;

allyl; or propargyl; or one of $R^2$ and $R^3$ is hydrogen and the other is hydroxy, or

—$NH_2$.

The more preferred 9a-azalides are selected from azithromycin (which is 9-deoxo-9a-aza-9a-methyl-9a-homoerythromycin A), 4"-epi-azithromycin, 4"-deoxy-4"-aminoazithromycin, and 4"-epi-4"-deoxy-4"-aminoazithromycin.

In another preferred embodiment, the present invention provides a method for the treatment or prevention of bovine or swine bacterial respiratory infections wherein the causative organism is selected from a group consisting of *Pasteurella* spp., an *Actinobacillus* spp., *Haemophilus somnus* and *Mycoplasma* spp., which comprises administering to a cattle or swine in need of such treatment or prevention a therapeutically or prophylactically effective amount of an 9a-azalide. More preferably, the 9a-azalide is of formula I; and particularly preferred are 9a-azalides selected from azithromycin, 4"-epi-azithromycin, 4"-deoxy-4"- aminoazithromycin, and 4"-epi-4"-deoxy-4"-aminoazithromycin.

In another preferred embodiment, the present invention provides a method for the treatment or prevention of bovine or swine bacterial enteric infections wherein the causative organism is selected from *Escherichia coli, Treponema hyodysenteriae*, and Salmonella spp., which comprises administering to a cattle or swine in need of such treatment or prevention a therapeutically or prophylactically effective amount of an 9a-azalide. More preferably the 9a-azalide is of formula I; and particularly preferred are 9a-azalides selected from azithromycin, 4"-epi-azithromycin, 4"-deoxy-4"-aminoazithromycin, and 4"-epi-4"-deoxy-4"-aminoazithromycin.

As used herein "9a-azalide" means a compound having the following core structure in which the asterisks indicate sites for substitution:

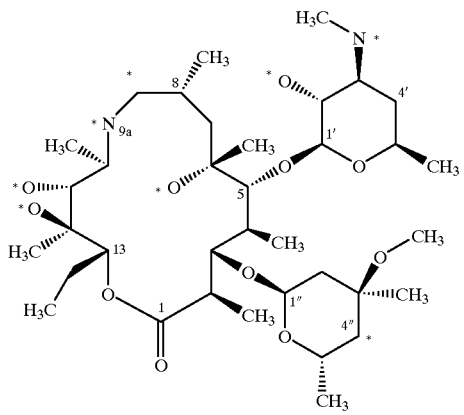

The 9a-azalides are named herein as derivatives of azithromycin, which is 9-deoxo-9a-aza-9a-methyl-9a-homoerythromycin A.

The term "therapeutically or prophylactically effective amount" means that amount of an 9a-azalide that will provide a level of antibacterial activity at the target site of infection that is sufficient to inhibit the bacteria in a manner that allows the host animal to overcome or be protected from the infection.

"Treatment or prevention" means use of 9a-azalide following or prior to manifestation of signs and symptoms suggestive of bacterial infection to allow the host animal to overcome or be protected from the infection.

"Bacterial respiratory or enteric infections" means infections of the respiratory or digestive tract for which the causative organism or the likely causative organism is susceptible to 9a-azalide. Such organisms include, but are not limited to, Pasteurella species (e.g. *P. haemolytica, P. multocida*), *Haemophilus somnus, Actinobacillus pleuropneumoniae*, Mycoplasma spp., *E. coli, Treponema hyodysenteriae*, and Salmonella spp. (e.g. *S. typhimurium, S. dublin*).

The term "pharmaceutically acceptable salts" refers to salts prepared from pharmaceutically acceptable non-toxic acids including inorganic acids and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

9a-Azalides are either known compounds, such as those disclosed in the patents and published patent applications cited hereinabove, or they may be prepared from readily available starting material using conventional chemical synthesis methods.

9a-Azalides may be administered to a host in need of treatment for, or prevention of bacterial respiratory or enteric diseasease in a manner similar to that used for other antibacterial agents; for example, 9a-azalides may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of bacterial diseases, the oral dosage may range from 1 mg/kg to 1000 mg/kg; and the parenteral dosage may range from 0.01 mg/kg to 500 mg/kg. For prophylactic use in animals, the oral dosage may range from 1 mg/kg to 1000 mg/kg; and the parenteral dosage may range from 0.01 mg/kg to 500 mg/kg. The 9a-azalides of the present invention are preferably administered parenterally at a dosage range of about 0.1 to about 10 mg/kg.

The 9a-azalides are preferably used in a pharmaceutical composition comprising the active ingredient and an inert pharmaceutically acceptable carrier. The pharmaceutical compositions of the present invention comprise an 9a-azalide as an active ingredient, and may also contain a pharmaceutically acceptable carrier and optionally other therapeutic ingredients. The formulations include compositions suitable for oral, rectal, topical, and parenteral (including subcutaneous, intramuscular, and intravenous) administrations, although the most suitable route in any given case will depend on the particular host, and nature and severity of the conditions for which the active ingredient is being administered. The pharmaceutical compositions may be conveniently presented in unit dosage form and prepared by any of the methods well-known in the art of pharmacy.

In practical use, the 9a-azalide can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous, intramuscular, and subcutaneous); generally parenteral administration is preferred.

In preparing the compositions for oral dosage form, any of the usual pharmaceutical media may be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, 9a-azalides may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5–10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

Compositions containing an 9a-azalide may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals.

The pharmaceutical composition containing 9a-azalide may optionally contain a second active ingredient, a biological component such as an antigen, or a dietary supplement such as minerals or vitamins. Active ingredients may include immunomodulators such as interferon, interleukins and other chemokines, non-steroidal antiinflammatories such as propionic acid derivatives (e.g. ibuprofen, ketoprofen, naproxen, benoxprofen, carprofen), acetic acid derivatives (e.g. acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (e.g. flufenamic acid, meclofenamic acid, mefenamic acid, niflumic acid and tolfenamic acid), biphenylcarboxylic acids (e.g. diflufenisal, flufenisal), and cyclooxygenase-2 (COX-2) inhibitors, and antiparasitic agents such as avermectin, ivermectins, milbemycins, levamisole, benzimidazoles, pyrantevmorantel. Biologicals may be vaccines commonly used in the livestock industry against infectious bovine rhinotracheitis, bovine virus diarrhea, respiratory syncythial virus, parainfluenza, transmissable gastroenteritis, porcine reproductive and respiratory syndrome, rotavirus, and coronavirus. Dietary supplements may be vitamins, iron, selenium, and the like.

The following examples are provided to more fully illustrated the present invention, and are not be construed as limiting the scope of the claims in any manner.

IN VITRO ACTIVITY OF 9a-AZALIDES

The antibacterial activity of representative 9a-azalides against a panel of veterinary pathogens was determined by the minimum inhibitory concentration (MIC) method well known in the art. This is done by preparing a series of culture tubes, each containing a medium with a different concnetration of the antimicrobial agent, and inoculating all the tubes with the same organism. The lowest concentration of agent that completely prevents the appearance of turbidity is noted, and this concentration is called the MIC.

The range of antibacterial activity of azithromycin and 4"-deoxy-4"-aminoazithromycin against key veterinary organisms is summarized below:

| Organism | MIC range ($\mu$g/ml) |
| --- | --- |
| P. haemolytica | 0.125–0.5 |
| P. multocida | 0.125–2 |
| H. somnus | 0.062–0.25 |
| A. pleuropneumoniae | 0.062–0.5 |
| E. coli | 0.5–16 |
| Salmonella spp. | 1–16 |

What is claimed is:

1. A method for the treatment or prevention of bacterial respiratory infection caused by a Pasteurella spp., Actinobacillus spp., *Haemophilus somnus*, or Mycoplasma spp. or enteric infection caused by *Treponema hyodysenteriae* in a livestock animal which comprises administering to a livestock animal in need of such treatment or prevention a therapeutically or prophylactically effective amount of a 9a-azalide.

2. The method of claim 1 wherein the 9a-azalide has the formula I:

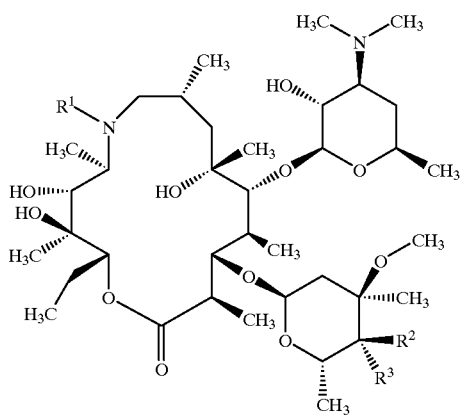

or a pharmaceutically acceptable salt thereof, or a pharmaceutically acceptable metal complexes thereof, wherein said metal is selected from the group consisting of copper, zinc, cobalt, nickel and cadmium; where $R^1$ is hydrogen;

$C_{1-3}$ alkyl optionally substituted by hydroxy, $C_{1-3}$ alkoxy, cyano, $C_{1-3}$ alkoxycarbonyl, halogen, amino, $C_{1-3}$ alkylamino, or di($C_{1-3}$ alkyl)amino;

allyl; or propargyl; and one of $R^2$ and $R^3$ is hydrogen and the other is hydroxy, or

—$NH_2$.

3. The method of claim 2 wherein the 9a-azalide is selected from the group consisting of azithromycin, 4"-epi-azithromycin, 4"-deoxy-4"-aminoazithromycin, and 4"-epi-4"-deoxy-4"-aminoazithromycin.

4. The method of claim 1 wherein said bacterial infection is bovine or swine respiratory infection.

5. The method of claim 2 wherein said bacterial infection is bovine or swine respiratory infection.

6. The method of claim 3 wherein said bacterial infection is bovine or swine respiratory infection.

7. The method of claim 1 wherein said bacterial infection is bovine or swine enteric infection.

8. The method of claim 2 wherein said bacterial infection is bovine or swine enteric infection.

* * * * *